(12) United States Patent
Hayes-Gill et al.

(10) Patent No.: US 10,898,097 B2
(45) Date of Patent: Jan. 26, 2021

(54) APPARATUS AND METHOD FOR DETECTING AN ABDOMINAL ELECTROPHYSIOLOGICAL SIGNAL

(71) Applicant: Monica Healthcare Limited, Nottingham (GB)

(72) Inventors: Barrie Robert Hayes-Gill, Nottingham (GB); Jean-Francois Pieri, Nottingham (GB)

(73) Assignee: Monica Healthcare Limited, Nottingham (GB)

(*) Notice: Subject to any disclaimer, the term of this patent is extended or adjusted under 35 U.S.C. 154(b) by 674 days.

(21) Appl. No.: 15/029,447

(22) PCT Filed: Oct. 17, 2014

(86) PCT No.: PCT/GB2014/053120
§ 371 (c)(1),
(2) Date: Apr. 14, 2016

(87) PCT Pub. No.: WO2015/056027
PCT Pub. Date: Apr. 23, 2015

(65) Prior Publication Data
US 2016/0262649 A1    Sep. 15, 2016

(30) Foreign Application Priority Data
Oct. 17, 2013 (GB) .................................. 1318413.0

(51) Int. Cl.
*A61B 5/04* (2006.01)
*A61B 5/0448* (2006.01)
(Continued)

(52) U.S. Cl.
CPC .......... *A61B 5/0448* (2013.01); *A61B 5/0006* (2013.01); *A61B 5/0245* (2013.01);
(Continued)

(58) Field of Classification Search
USPC ......................... 600/372, 382–393, 508–509
See application file for complete search history.

(56) References Cited

U.S. PATENT DOCUMENTS

| | | | |
|---|---|---|---|
| 4,945,911 A | 8/1990 | Cohen et al. | |
| 4,947,846 A * | 8/1990 | Kitagawa | A61B 5/0408 600/391 |

(Continued)

FOREIGN PATENT DOCUMENTS

| | | |
|---|---|---|
| CA | 2 063 691 A1 | 9/1992 |
| CN | 101790347 A | 7/2010 |

(Continued)

OTHER PUBLICATIONS

Patent Cooperation Treaty, International Search Report and ISA Written Opinion on PCT/GB2014/053120, dated Mar. 31, 2015.
(Continued)

*Primary Examiner* — Joseph A Stoklosa
*Assistant Examiner* — Brian M Antiskay
(74) *Attorney, Agent, or Firm* — Andrus Intellectual Property Law, LLP (57) ABSTRACT

The invention concerns a multi-electrode patch for abdominal electrophysiological detection. The patch has a flexible substrate interconnecting multiple electrodes and a module unit for removably engaging with an electronic readout device for detecting a maternal and/or fetal electrophysiological signal from the electrodes. The module has a mechanical module unit for removable mechanical engagement with a housing of the readout device, and an electrical module unit for making an electrical connection from the electrodes to the readout device. Engaging the patch with the readout device comprises engaging both the mechanical module unit and the electrical module unit. The patch may be flexible in a manner that allows variation in the relative positioning between the electrodes. The patch and/or elec- (Continued)

tronic readout device may comprise a security device for communication of an authentication code.

34 Claims, 6 Drawing Sheets

(51) Int. Cl.
  *A61B 5/00*     (2006.01)
  *A61B 5/024*    (2006.01)
  *A61B 5/0444*    (2006.01)
  *A61B 5/0245*    (2006.01)
  *A61B 5/044*    (2006.01)
  *A61B 5/08*     (2006.01)
  *A61B 5/0408*    (2006.01)

(52) U.S. Cl.
  CPC ......... *A61B 5/02411* (2013.01); *A61B 5/044* (2013.01); *A61B 5/0444* (2013.01); *A61B 5/08* (2013.01); *A61B 5/4356* (2013.01); *A61B 5/4362* (2013.01); *A61B 5/6833* (2013.01); *A61B 5/6848* (2013.01); *A61B 5/04085* (2013.01); *A61B 5/04087* (2013.01); *A61B 2560/045* (2013.01); *A61B 2560/0456* (2013.01); *A61B 2562/08* (2013.01)

(56) References Cited

U.S. PATENT DOCUMENTS

| | | | |
|---|---|---|---|
| 5,458,124 A | 10/1995 | Stank et al. | |
| 6,117,077 A * | 9/2000 | Del Mar | A61B 5/04085 600/300 |
| 6,415,169 B1 * | 7/2002 | Kornrumpf | A61B 5/04085 600/382 |
| 6,605,046 B1 * | 8/2003 | Del Mar | A61B 5/04085 600/507 |
| 6,816,744 B2 | 11/2004 | Garfield et al. | |
| 6,847,836 B1 * | 1/2005 | Sujdak | A61B 5/04085 600/382 |
| 6,856,832 B1 * | 2/2005 | Matsumura | A61B 5/0006 128/903 |
| 7,616,980 B2 | 11/2009 | Meyer | |
| 8,740,825 B2 * | 6/2014 | Ehrenreich | A61H 1/00 601/47 |
| 8,880,140 B2 | 11/2014 | Hayes-Gill | |
| 9,351,682 B2 * | 5/2016 | Euliano, II | A61B 5/7278 |
| 2002/0107435 A1 * | 8/2002 | Swetlik | A61B 5/0006 600/382 |
| 2002/0193670 A1 | 12/2002 | Garfield et al. | |
| 2004/0054393 A1 * | 3/2004 | Stemme | A61B 5/04025 600/372 |
| 2004/0176674 A1 * | 9/2004 | Nazeri | A61B 5/0006 600/382 |
| 2005/0251002 A1 * | 11/2005 | Istvan | A61B 5/0006 600/393 |
| 2007/0027388 A1 * | 2/2007 | Chou | A61B 5/0002 600/393 |
| 2007/0260133 A1 * | 11/2007 | Meyer | A61B 5/04085 600/393 |
| 2008/0114220 A1 * | 5/2008 | Banet | A61B 5/021 600/301 |
| 2008/0138583 A1 | 6/2008 | Bhandari et al. | |
| 2008/0177168 A1 | 7/2008 | Callahan et al. | |
| 2008/0243207 A1 | 10/2008 | Corndorf | |
| 2009/0054737 A1 | 2/2009 | Magar et al. | |
| 2009/0259133 A1 * | 10/2009 | Wolfberg | A61B 5/412 600/511 |
| 2010/0274099 A1 | 10/2010 | Telfort et al. | |
| 2011/0021937 A1 | 1/2011 | Hugh et al. | |
| 2011/0028822 A1 * | 2/2011 | Beck | A61B 5/0408 600/386 |
| 2011/0098583 A1 * | 4/2011 | Pandia | A61B 5/029 600/508 |
| 2011/0112440 A1 | 5/2011 | Euliano, II et al. | |
| 2011/0118584 A1 * | 5/2011 | Gratteau | A61B 5/0496 600/383 |
| 2011/0306862 A1 * | 12/2011 | Hayes-Gill | A61B 5/04085 600/382 |
| 2012/0071744 A1 | 3/2012 | Euliano, II et al. | |
| 2012/0232398 A1 | 9/2012 | Roham et al. | |
| 2013/0234830 A1 | 9/2013 | Brumer | |
| 2013/0345539 A1 * | 12/2013 | Quintanar | A61B 5/04085 600/385 |
| 2015/0087949 A1 * | 3/2015 | Felix | A61B 5/04087 600/382 |
| 2016/0066879 A1 * | 3/2016 | Telfort | A61B 5/6843 600/484 |
| 2016/0128594 A1 * | 5/2016 | Amir | A61B 5/0006 600/382 |
| 2016/0150989 A1 * | 6/2016 | Felix | A61B 5/04017 600/523 |

FOREIGN PATENT DOCUMENTS

| | | |
|---|---|---|
| CN | 101969840 A | 2/2011 |
| CN | 102499667 A | 6/2012 |
| EP | 1 905 354 A1 | 4/2008 |
| EP | 1182965 B1 | 4/2008 |
| EP | 1905354 A1 | 4/2008 |
| JP | 63-314473 A | 12/1988 |
| JP | 02-068803 U1 | 5/1990 |
| JP | 06-038938 A | 2/1994 |
| JP | 2003-520094 A | 7/2003 |
| JP | 2007-301358 A | 11/2007 |
| JP | 2011-514826 A | 5/2011 |
| JP | 2011-516110 A | 5/2011 |
| JP | 2012-519022 A | 8/2012 |
| JP | 2013-066526 A | 4/2013 |
| RU | 2 108 059 C1 | 4/1998 |
| RU | 2 387 370 C2 | 4/2010 |
| WO | 86/02250 A1 | 4/1986 |
| WO | 03055387 A1 | 7/2003 |
| WO | 2007/095457 A2 | 8/2007 |
| WO | 2007095457 A2 | 8/2007 |
| WO | 2008-016151 A1 | 2/2008 |
| WO | 2008048760 A1 | 4/2008 |
| WO | 2009146181 A1 | 12/2009 |

OTHER PUBLICATIONS

United Kingdom Intellectual Property Office, Combined Search and Examination Report on GB1318413.0, dated Apr. 20, 2015.
Griss, P., et al., "Spiked Biopotential Electrodes", Proceedings Ieee Thirteenth Annual International Conference on Micro Electro Mechanical Systems, pp. 323-328 (Jan. 23, 2000).
Examination Report issued in connection with corresponding AU Application No. 2014335892 dated May 25, 2018, 4 pages.
Office Action and Search Report issued in connection with corresponding RU Application No. 2016118407 dated Jun. 28, 2018, 22 pages.
First Office Action and Search issued in connection with corresponding CN Application No. 201480065751.X dated Jul. 19, 2018, 34 pages.
Notification of Reasons for Refusal issued in connection with corresponding JP Application No. 2016-524442 dated Sep. 18, 2018, 10 pages.
Office Action and Search Report issued in connection with corresponding RU application No. 2016118407 dated Jan. 25, 2019; 11 pages.
European patent application 14790681.2 filed May 17, 2016—Examination Report dated Jun. 26, 2020; 7 pages.

* cited by examiner

*Figure 1*

PIN 1 - SHIELD
PIN 2 - PAD 4
PIN 3 - PAD 5
PIN 4 -
PIN 5 - PAD 1
PIN 6 - PAD 2
PIN 7 - PAD 3
PIN 8 - SHIELD

APPARATUS AND METHOD FOR DETECTING AN ABDOMINAL ELECTROPHYSIOLOGICAL SIGNAL

The present invention relates to a method and apparatus for detecting abdominal electrophysiological signals. More specifically, the present invention relates to an apparatus or method for detecting at least one of: a maternal electrocardiogram, a fetal electrocardiogram, a maternal heart rate, a fetal heart rate, and uterine activity, and preferably a method or apparatus for detecting at least 2 or 3, or all of the above.

Medical devices are known that can be used to detect a fetal electrocardiogram (fECG) without making physical contact with the fetus. Such devices use electrodes that are placed on the mother's skin to detect electrophysiological signals. The maternal electrocardiogram (mECG) will also tend to be detected by the electrodes, and it can be challenging to separate the fECG from the mECG. The electrical signals detected by the electrodes can be processed to determine: the fetal heart rate (from the fECG), the maternal heart rate (from the mECG). Maternal contractions, often referred to as uterine activity (UA) can be determined by electrohysterography (changes in electrical potential due to uterine contractions).

WO2009/150440 (Monica Healthcare) discloses a multi-electrode patch for use in fetal heart rate monitoring, the patch comprising a flexible substrate attachable to the skin of a pregnant subject. Three sensing electrodes are positioned on the flexible substructure to approximate an arc that is substantially the same length as the arc formed by a uterus fundus of a pregnant subject. Connection ports are provided by which each sensing electrode may be connected to a fetal heart rate monitor which receives the electrical signals from the electrodes and determines the fetal heart rate from the fECG. A multi-electrode patch is disclosed that includes integrated circuitry configured to amplify and filter a detected fECG signal.

EP 1 854 403 (Meyer) discloses a radial electrode assembly for monitoring fECG and mECG signals. The assembly comprises a flexible substrate defining a central focal point, and a plurality of electrodes disposed on the periphery of the flexible substrate, at a substantially equal fixed radial distance from the focal point.

Although the patches disclosed in the prior art for fECG detection are promising, considerable room for improvement remains.

A fixed patch arrangement results in a precise fixed spacing between the electrodes. This fixed electrode spacing is advantageous for repeatability of measurements, but limits the degree of flexibility in electrode placement. The optimum electrode location may, for instance, vary as a function of the size of the fetus and/or mother. The size of the fetus clearly varies as a function of gestational age. Furthermore, the fixed distance between electrodes of a patch arrangement does not accommodate movement of the subject (for example resulting from locomotion or breathing) in the same way that individual electrodes connected by leads to a signal processing unit can.

In arrangements for fECG which use a readout circuit that is separate from the electrodes, the wires or leads that electrically connect the electrodes to the readout circuit can also result in problems. One such problem is that of noise from the leads. Such noise may arise from a number of sources, including electromagnetic interference, cable microphony, and triboelectric effects. Furthermore, the leads are typically re-used, which present possible issues with cross infection.

Although fECG patches with integrated electronics can address some of the problems associated with cables, a further problem with fECG patches that include integrated electronics is that this greatly increases the cost of each patch. This can make them too expensive for routine monitoring applications, or can limit the sophistication of the electronics of the readout, compromising performance. The patches are often disposable single use patches.

Another problem with obtaining high quality abdominal electrophysiological signals is that of making a good electrical contact with the skin of the subject. This is presently achieved by abrasion of the highly resistive stratum corneum, so as to make contact with the less resistive skin layers below. This skin preparation can be uncomfortable for the subject, and takes time and skill from the user of the apparatus.

It is an object of the present invention to ameliorate or overcome at least some of the above mentioned problems.

According to a first aspect of the present invention, there is provided: a multi-electrode patch for abdominal electrophysiological detection, the patch comprising: a flexible substrate interconnecting a plurality of electrodes, and a flexible substructure, wherein the electrodes are moveable or conformable to a surface such that the relative positions of at least some of the electrodes on the surface relative to each other can be adjusted by moving the electrodes and deforming the flexible substructure.

The position of each electrode may be moveable so that a position of the each electrode can be adjusted to conform to the surface. Each electrode may be substantially rigid. The surface may be non-planar.

The flexible substrate is preferably a unitary item (single part). The flexible substrate is preferably formed by printing a circuit onto a flexible support.

Elongate conductors may extend along and/or be embedded in the flexible substrate and may depend from the electrodes. The conductors may or may not extend towards a common or central connector region of the patch. One or more via may be provided in the electrical substrate to define a conductor path, for example between one side of the flexible substrate and an opposing side. One or more via may be provided in a flexible support and/or the flexible substructure. Thus electrical signals may be communicated from an electrode on a side of the patch adjacent a wearer's skin in use to an opposing side, which faces away from the wearer.

The circuit and/or conductors of the flexible substrate may comprise silver. A silver-containing ink may be used to print the conductors/circuit. Matching of the conducting material properties with a suitable flexible substrate material, such as a polymer has been found to be important in preventing breakage/discontinuity in the conducting material through use of the patch. A Polyethylene terephthalate (PET) substrate layer may be used.

The flexible substrate may comprise the electrodes, so that the electrodes are formed integrally with the flexible substrate.

The ability to adjust the spacing between electrodes addresses two problems. Firstly, the patch can be made more comfortable for the subject, by accommodating movement of the subject (e.g. as a result of breathing or locomotion). Secondly, the patch can be reconfigured to provide a more optimal placement of the electrodes for the specific subject to be tested.

The flexible substructure may comprise an arched, curved or serpentine elongate portion. The flexible substructure may comprise features that are at least one of: convoluted, folded, nested, zig-zag, elongate and indirect. Elongate, narrow features that extend in a direction at an angle to the desired direction of compliance are preferably used. These are convenient and practical ways to provide a flexible substructure that can allow repositioning of one or more electrode relative to a central or common portion of the substrate. A serpentine portion has the advantage of being a compact way of providing a highly compliant substructure, which can be arranged to have a substantially linear stiffness over a relatively long displacement distance.

The flexible substructure may comprise a corrugated portion (in the Z-direction relative to the surface or subject's abdomen, in use). This provides a useful alternative to flexible substructures formed by changing the layout of the substrate (in plan view).

The patch, or at least a portion thereof, may remain substantially conformed to the surface as the relative position of at least some electrodes is adjusted. One or more electrode may be arranged on an elongate or arm portion of the patch which may depend from a common or central patch portion. A hinge, crease, line of weakness or other formation to promote flexing away from the plane of the patch may be provided in the patch or substrate between an electrode and the common/central patch portion. Such formation may be provided at an arm portion of the patch. Thus one electrode can be raised and repositioned independently of the remainder of the patch or other electrodes. In one example the formation comprises a line or region in which no adhesive is provided.

The electrodes may comprise a common electrode and a plurality of sensing electrodes, the sensing electrodes being spaced apart from the common electrode and each other.

The patch may further comprise a drive electrode, for applying a voltage (other electrodes being sensing electrodes for sensing a voltage and/or current).

The flexible substructure may be disposed between the common electrode and the sensing electrodes, so that the position of the common electrode on the surface can be adjusted relative to that of the sensing electrodes. Each sensing electrode may be connected to common, electrode by a respective flexible substructure. Alternatively, one or more sensing electrodes may be fixedly connected to the common electrode.

The flexible substructure may be disposed between at least two of the sensing electrodes. This allows them to be positioned with varying distances between them in use, and accommodates relative movement of their attachment points (on the subject).

At least one further flexible substructure may be provided between at least two of the sensing electrodes.

The sensing electrodes may be disposed along an arc, with a first sensing electrode at one end of the arc, a third sensing electrode at the other end of the arc, and a second sensing electrode on the arc, between the first and third sensors; wherein a first flexible substructure is arranged to allow the distance along the surface between the first and second sensing electrode to vary, and a second flexible substructure is arranged to allow the distance along the surface between the third and second sensing electrode to vary.

A flexible substructure may be associated with each electrode, so that the position of each electrode is adjustable by deforming its respective flexible substructure.

The flexible substrate may further comprise a reference feature for alignment with an umbilicus, and the flexible substructure allows the distance along the surface from the reference feature to at least one electrode to be adjusted. The reference feature may comprise a through hole in the substrate, or a partially transparent region, or a detent or point in the layout of the substrate.

An adhesive region may be provided, adjacent to the reference feature and/or at a central region of the patch, so that the patch and/or reference feature may be secured to the surface by the adhesive region. Each electrode may comprise an adhesive region, for example adjacent or encircling the electrode itself.

The flexible substrate may comprise a conducting layer and an insulating layer, and a graphite layer between the conducting layer and the insulating layer. The graphite layer may be arranged to reduce triboelectric charging as a result of interactions between the conducting layer and the insulating layer.

According to a second aspect of the invention, there is provided a multi-electrode patch for abdominal electrophysiological detection, the patch comprising: a flexible substrate that comprises a conducting layer and an insulating layer, and a graphite layer disposed between the conducting layer and the insulating layer. The graphite layer may reduce triboelectric effects arising from the interaction between the insulating layer and conducting layer.

The patch may comprise a plurality of conducting layers, the plurality of conducting layers comprising: a signal layer, for communicating electrical signals from the electrodes; and a shield layer, for shielding the signal layer from electromagnetic interference; and the shield layer may be separated from the signal layer by the graphite layer and the insulating layer.

The shield layer may be disposed adjacent to a first side of the signal layer, and the plurality of conducting layers may comprise a further shield layer disposed adjacent to a second side of the signal layer, and the further shield layer may be separated from the signal layer by a further graphite layer and a further insulating layer.

An outer insulating layer may be disposed adjacent to an outward facing side (e.g. in use of the patch) of at least one of the shield layer and further shield layer.

At least one electrode may comprise a plurality of biocompatible electrically conductive needles, wherein each needle has a length of between 10 µm and 200 µm. A biocompatible material is one that does not have a deleterious or injurious effect on a biological system as a result of it being used as intended. Examples of biocompatible materials for the conductive needles are doped silicon and gold coated plastics materials such as polycarbonates.

According to a third aspect of the invention, there is provided an electrode for a patch according to any other aspect of the invention, wherein the electrode comprises a plurality of biocompatible electrically conductive needles having a length of between 10 µm and 200 µm. Preferably the electrode comprises at least 1000 needles.

Using an electrode comprising electrically conducting biocompatible needles allows a good electrical contact to be made with the skin without the need for careful skin preparation before applying the electrodes. The skin preparation may comprise simply wiping the skin with an anti-septic or anti-bacterial wipe, or there may be no skin preparation.

The plurality of biocompatible needles may have a length between 20 µm and 100 µm. This range of lengths is long enough to penetrate the typical thickness of the highly insulating stratum corneum so as to make electrical contact with the more conductive underlying layers, but not long enough to stimulate nerves so as to cause pain.

Each of the plurality of biocompatible needles may have a mean diameter of between 10 µm and 100 µm. This range of diameters is a good compromise between manufacturability, sharpness and robustness. The needle may taper (for example, as a result of a wet etch following a silicon crystal plane).

The areal density of the needles may be between 200 and 1000 needles per square millimetre, preferably between 400 and 600 needles per square millimetre.

The needles may be configured to penetrate the median thickness of the stratum corneum of the abdomen of a pregnant human.

An module unit may be provided (with any aspect of the invention) for removably engaging with an electronic readout device for detecting a fetal heart rate from the electrodes; wherein the module unit comprises a mechanical module unit for removable mechanical engagement with a housing of the readout device, and an electrical module unit for making an electrical connection from the electrodes to the readout device; and wherein engaging the patch with the readout device comprises engaging both the mechanical module unit and the electrical module unit.

According to a fourth aspect of the invention, there is provided a multi-electrode patch for abdominal electrophysiological detection, the patch comprising: a flexible substrate interconnecting a plurality of electrodes; and a module unit for removably engaging with an electronic readout device for detecting a maternal and/or fetal electrophysiological signal from the electrodes; wherein the module comprises a mechanical module unit for removable mechanical engagement with a housing of the readout device, and an electrical module unit for making an electrical connection from the electrodes to the readout device; and wherein engaging the patch with the readout device comprises engaging both the mechanical module unit and the electrical module unit.

Using a patch with such a module allows the use of removable readout circuit. This provides all of the advantages of an integrated readout circuit, including reduced cable noise and increased freedom of movement when wearing the patch, but without many of the drawbacks (e.g. increased patch cost, compromised readout electronics due to the need to control costs), because the removable readout circuit is re-usable.

The mechanical module unit may comprise a magnet or ferromagnetic material.

The mechanical module unit may comprise a cradle connected to the flexible substrate that is mechanically engaged with the housing by sliding at least part of the housing into the cradle.

The module unit may be disposed between, and preferably substantially equidistant from, at least two electrodes. In such a manner the device is positioned typically at the centre of gravity of the flexible structure.

The electrical module unit may comprise a plurality of electrical contacts on the flexible substrate.

The electrical connection between the module unit and the readout device may comprise one or more resilient contact member, which is typically a conductor, on one or more of the patch substrate, electrical module unit or readout device. The resilient contact member may comprise a spring contact or other resiliently deformable contact.

A compression seal may be provided on the module unit or readout device, for example on the housing thereof. The seal may surround or otherwise isolate the electrical connection, for example in a waterproof manner.

The patch may comprise a security device for providing an authentication code associated with the patch to an electronic readout device for detecting a fetal heart rate from the electrodes, so as to prevent use of the readout device with: a patch that does not include the security device, or a patch that provides the wrong authentication code. Furthermore the security device may provide a unique patient ID that ensures patient data is not compromised or confused with other patients in the hospital, health centre or at home within the community. Alternatively, the authentication code associated with the patch may be linked with a unique patient ID so that the patient ID can be identified from the authentication code of the patch.

According to a fifth aspect of the invention, a multi-electrode patch is provided for abdominal electrophysiological detection, the patch comprising: a flexible substrate interconnecting a plurality of electrodes; and a security device for electrically authenticating the patch to an electronic readout device for detecting the fetal electrocardiogram from the electrodes, so as to prevent use of the readout device with a patch that does not include the security device.

The use of electronic authentication between the patch and the readout circuit prevents the use of inferior patches with the readout circuit thereby providing greater control over the performance of the combined readout circuit and patch system (improving safety). Furthermore, they facilitate control over supply of compatible patches, so that a vendor of apparatus for electrophysiological monitoring can be certain that only consumables of appropriate quality are used in the system.

According to a sixth aspect of the invention, an electronic readout device is provided for use with a patch according to an embodiment to amplify and filter at least one signal from the electrodes of the patch, the readout device comprising: an electrical power source for storing and providing electrical power to the device; a housing having a mechanical module for mechanical engagement with the mechanical module unit of the patch; and an electrical module unit for electrical engagement with the electrical module unit of the patch.

Such a readout device may be considerably more convenient than a readout device that is connected to the patch via a cable, and is further advantageous in that lead noise is substantially reduced.

The mechanical module unit of the housing may comprise a magnet or ferromagnetic material.

The electrical module unit of the readout device may comprise at least one contact mounted on a resiliently deformable element.

The readout device may be configured to determine at least one of: a fetal heart rate, a fetal ECG, a maternal heart rate, a maternal ECG, and uterine activity, or two or three or four or all five of them.

The readout device may comprise a wireless transmitter, for transmitting information derived from the signal.

The readout device may be operable to transmit an output, e.g. via the wireless transmitter, the output comprising at least one of: a fetal heart rate, a fetal ECG, a maternal heart rate, a maternal ECG, and uterine activity.

The readout device may be configured to control the power of the wireless transmitter, based on at least one of a bit error rate at a receiver and a signal strength at the receiver. This enables far more efficient use of power, and consequently may greatly increase battery life for the readout device.

According to a seventh aspect of the invention, there is provided a multi-electrode patch for abdominal electrophysiological detection, comprising an inertial sensor.

The readout device may comprise an inertial sensor.

The inertial sensor may comprise at least one of an accelerometer or a gyroscope.

The inertial sensor may be configured to detect at least one of a maternal movement, maternal breathing, maternal contraction and fetal movement.

The readout device may be configured to use information from an inertial sensor to reduce artefacts in at least one of a fetal heart rate and a fetal ECG output from the readout device.

The readout device may comprise a security device that is arranged to prevent the readout device from functioning with the patch unless it receives an appropriate authentication code from a corresponding security device of the patch.

According to a eighth aspect of the invention, there is provided an electronic readout device for use with a patch according to an embodiment, to amplify and filter at least one signal from the electrodes of the patch, wherein the readout device comprises a security device that is arranged to prevent the readout device from functioning with the patch unless it receives appropriate authentication from the security device of the patch.

The readout device may be configured to store a patch authentication code associated with a particular patient, so that the readout device becomes operable only with a patch having an authentication code associated with a particular patient.

The readout device may be configured to detect an electrophysiological signal from the voltage between two sensing electrodes of the patch. The two sensing electrodes may be those that are intended to be placed laterally on either side of a median line of the subject, adjacent to the umbilicus.

According to an ninth aspect of the invention, there is provided a receiving and displaying station for receiving information from a readout device according to an embodiment, wherein the receiving and displaying station comprises: a display for displaying at least one of a fetal heart rate, a fetal ECG, a maternal heart rate, a maternal ECG, and uterine activity; and a dock area for receiving the housing of the readout device; wherein the dock comprises an inductive charger for charging the electrical power source of the readout device.

The display and dock may both be housed within a single housing enclosure.

The display station may be configured to transmit at least one of: a fetal heart rate, a fetal ECG, a maternal heart rate, a maternal ECG and uterine activity to a further monitoring or display station, such as a cardiotocograph display device. Existing infrastructure can thereby be used to display information derived from the electrophysiological signals detected by the patch.

According to a tenth aspect of the invention, there is provided a system for abdominal electrophysiological detection, comprising a patch according to an embodiment of the invention, and a readout device for use with the patch, wherein the readout device is operable to determine at least one of: a fetal heart rate, a fetal ECG, a maternal heart rate, a maternal ECG, and uterine activity.

The system may further comprise a receiving station for receiving and displaying information received from the readout device, the information comprising at least one of: a fetal heart rate, a fetal ECG, a maternal heart rate, a maternal ECG, and uterine activity.

According to an eleventh aspect of the invention, there is provided an abdominal electrophysiological detection kit, comprising a plurality of patches, and optionally one or more of: instructions to use the patches; and at least one package, packaging up the patches in a sterile multi-patch pack. The patch and/or readout device may be in accordance with any other aspect of the invention.

According to an twelfth aspect of the invention, there is provided a method of determining human abdominal electrophysiological signals, comprising using a patch according to an embodiment of the invention, comprising: applying the patch to the abdomen of a pregnant human subject, and using a readout circuit to detect electrophysiological signals via the electrodes of the patch, and preferably displaying an output derived from said signals.

The method may further comprise using the electrophysiological signals to determine at least one of a fetal heart rate, a fetal ECG, a maternal heart rate, a maternal ECG, and uterine activity, and such physiological signals may be displayed.

Applying the patch to the abdomen of the subject may comprise the following steps:
  securing the reference feature to the abdomen;
  subsequently applying each of the electrodes of the patch in turn to the abdomen.

Applying each electrode of the patch to the abdomen may comprise the following steps:
  applying the electrode to the skin;
  testing the impedance of the electrical connection between the electrode and the skin; and
  if the impedance is above a predetermined value:
    removing the electrode without detaching the reference feature or any other electrodes of the patch from the skin;
    preparing the skin to reduce the impedance thereof; and
    re-applying the electrode.

The method may comprise detecting an electrophysiological signal from a voltage difference between a sensing electrode and a common electrode, and detecting a further electrophysiological signal from a voltage difference between a pair of sensing electrodes.

The pair of sensing electrodes may be applied to the abdomen, spaced apart either side of the median line of the subject, adjacent to the umbilicus.

The method may comprise determining at least one of: uterine activity, a fECG, a mECG, taking account the electrophysiological signal obtained from the pair of sensing electrodes.

The method may comprise applying the patch electrodes to the abdomen of the subject without first preparing the skin by removing a region of the stratum corneum (for instance where the electrodes comprise a plurality of needles).

The method may comprise engaging mechanical and electrical interface units of the readout device with the interface unit of the patch.

The method may comprise using the readout circuit to electronically authenticate the patch using the security device of the patch and the security device of the readout device.

The method may comprise configuring at least one readout device to work with a particular patch, based on the authentication code of the patch. The method may comprise configuring more than one readout device to work with a particular patch, based on the authentication code of the patch. Rapid switching between readout devices may thereby be achieved, with one readout device in use on the patch, and at least one further readout device ready for use. The at least one readout device ready for use may, for instance, be left charging on a receiving station.

It will be appreciated that a number of essential or preferable features have been defined above in relation to one particular aspect of the invention for the sake of brevity.

However the optional features of each of the specific foregoing aspects and embodiments of the invention can be combined with other aspects of the invention, as appropriate, wherever practicable.

The invention will now be described, purely by way of example, with reference to the accompanying drawings, in which.

Figure 1:
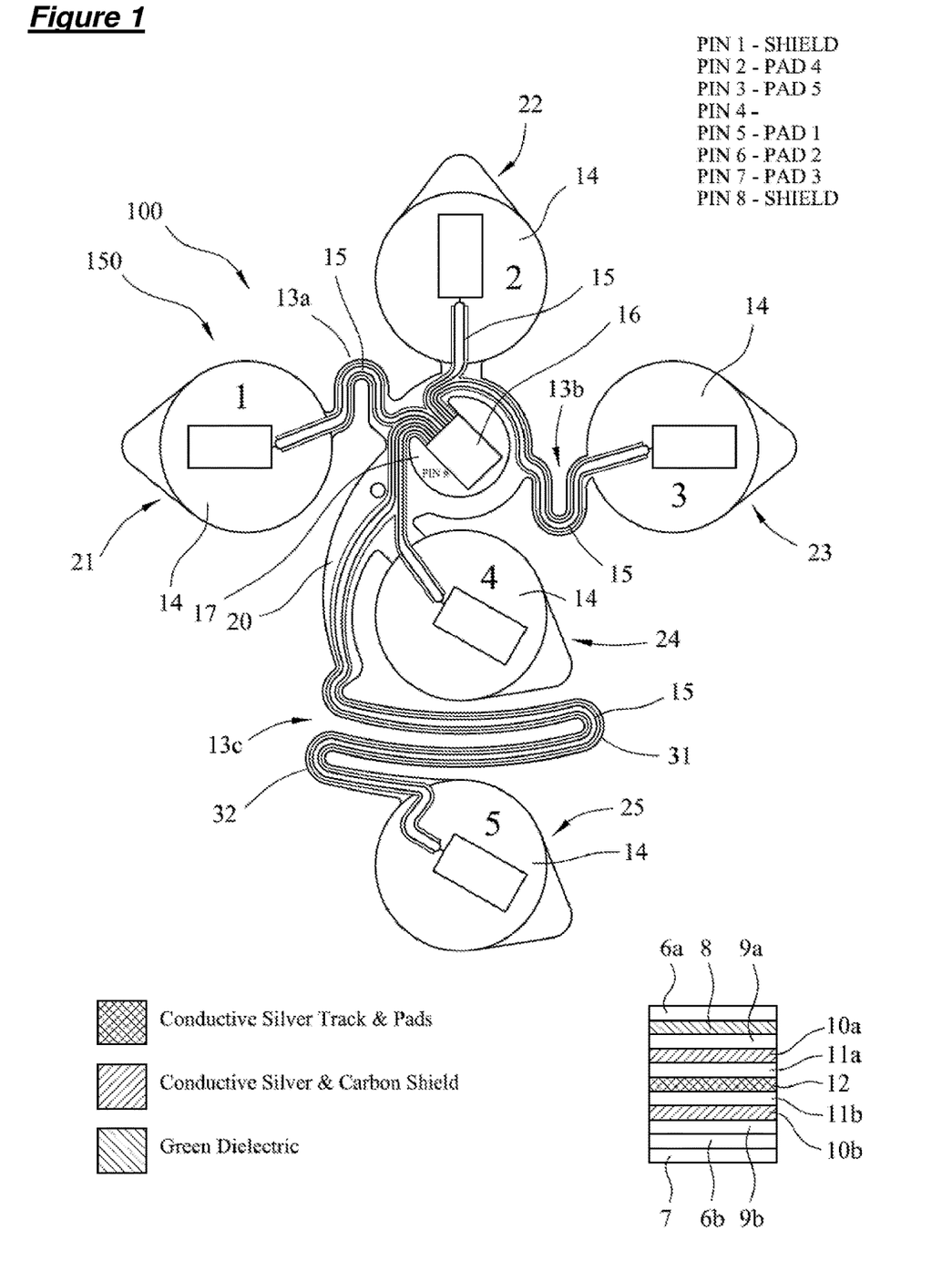
FIG. 1 is a layout diagram of a patch according to an embodiment of the invention.

Referring to FIG. 1, a patch 150 according to an embodiment is shown, comprising a flexible substrate 100, viewed from the side that is to be facing the abdomen, in use. The flexible substrate 100, comprises a plurality of layers 6-12. The layers 6-12 are patterned so as to define the shape of the substrate 100, and to form electrodes 1-5. Each electrode 1-5 is connected via a conducting track 15 to an electrical module unit 16, for electrically connecting the electrodes 1-5 to a readout device (not shown).

The electrodes 1-5 and/or the conducting tracks 15 are formed from the signal layer 12, which comprises silver. For example, the conducting film used can be silver chloride which provides a good stoichiometric match to saline based electrode gels. A silver-containing ink may be used in particular to print the conducting tracks 15 and/or signal layer 12.

An insulating dielectric layer 11a, 11b is arranged on each respective side of the signal layer 12. The insulating dielectric layers 11a, 11b have a similar pattern to the conducting tracks 15 of the signal layer 12. The insulating layers 11a, 11b substantially overlay the conducting tracks 15, and are oversized relative thereto. The insulating layers 11a, 11b completely cover the conducting tracks between the electrodes 1-5 and the electrical module unit 16, while leaving the signal layer 12 exposed in the electrode and electrical module unit 16 region.

A graphite layer 10a, 10b is in contact with each of the respective dielectric layers 11a, 11b. The graphite layers 10a, 10b substantially overlay the respective insulating layer 11a, 11b, and are oversized relative thereto.

A first conducting shield layer 9a is in contact with the graphite layer 10a, and a second conducting shield layer 9b is in contact with the optional graphite layer 10b. The first and second conducting shield layers 9a, 9b substantially conform to the shape of their respective graphite layers 11a, 11b. The graphite layers 10a, 10b may reduce triboelectric charging of the respective shield layers 9a, 9b.

In some embodiments the graphite layers 10a, 10b may be omitted.

A further insulating dielectric layer 8 is in contact with the first conducting shield layer 9a, and an insulating overlaminate 6a is in contact with this layer 8. An insulating base layer 6b is also in contact with the second conducting shield layer 9b. The overlaminate 6a and base layer 6b are configured to substantially encapsulate the other layers of the substrate, except in the region of the electrodes 1-5. In the region of the electrodes, the signal layer 12 is exposed so that the electrodes 1-5 can make contact with an underlying surface. The insulating overlaminate 6a and base layer 6b may comprise a plastics material, such as polyester. The insulating dielectric layers 8, 11a, 11b may comprise a plastics material, such as polyester or polyimide.

The base layer 6b defines the external shape of the flexible substrate 100, and includes a circular region corresponding with each electrode 1-5. The electrodes 1-5 are substantially rectangular, and are surrounded by each respective circular region 21-25. In will be appreciated that in other embodiments, the electrodes 1-5 can be any appropriate shape, such as circular, square or rectangular. The circular regions 21-25 may be provided with an adhesive film around their perimeter, so that the each circular region can be adhered to the skin of a subject. A conducting medium (such as ECG gel) is preferably disposed between each electrode 1-5 and the skin of the subject, thereby securely coupling each electrode 1-5 to the skin of the subject.

The conducting medium preferably comprises at least 9% (by mass) of an electrolyte such as sodium chloride or potassium chloride. The conducting medium (or gel) may be applied by a user (e.g. a nurse or doctor) to the subject's abdomen when applying the patch, or may be pre-existing on the patch when it is removed from packaging (not shown). The conducting medium may be retained in contact with the electrode by a sponge element (not shown). Each circular region 21-25 comprises a lobe, or flap, that is substantially free from adhesive film or conducting medium, protruding from the edge of the circular region 21-25. Each electrode 1-5 can thereby be detached from the subject by peeling the circular region 21-25 away from the subject by the lobe.

For any polymer layer described above, a PET material may be used and has been found to provide useful properties, i.e. resilience, for avoiding breakage of the signal layer 12 during flexing of the patch in use. The material thickness of the polymer/PET layer(s) may be matched to the properties of the signal conducting layer 12 to prevent deformation of the tracks in a manner that is likely to lead to a break in the signal layer 12.

Although not explicitly shown in the figures, a plurality of vias may be provided through one or more of the above described layers in order to allow signals to pass to/from either external surface of the patch. Thus electrical signals may pass from the electrodes to the signal layer 12 and may pass form the signal layer 12 to the module unit 16 on the exterior of the patch substrate by way of a via formation passing through the intermediate layers.

The substrate 100 comprises a reference feature 17, for lining up with an umbilicus or other suitably recognisable feature of the subject. In this case, the reference feature 17 is defined by an aperture in the flexible substrate 100. In other embodiments the reference feature 17 may be a vertex, pointer or transparent region forming in the flexible substrate 100. The reference feature 17 may be associated with an adjacent adhesive region, by which the reference feature 17 can be secured to the subject, for example adjacent to the umbilicus.

The structure lends itself to a straightforward method of application. For example, the reference feature 17 may be secured at a reference point on the patient using the associated adhesive region. The electrodes 1-5 can subsequently be moved away from the abdomen to prepare the skin. For example each electrode 1-5 can then be placed in turn around the abdomen with, if necessary, suitable abrasive skin preparation. Once any skin preparation and the subsequent placement of an electrode 1-5 has been completed the impedance of the connection between the electrode 1-5 and the patient may be measured by an electronic readout device 200 (shown in FIG. 7). If the impedance is above a desired value, further preparation of the skin may be carried out to reduce the impedance to below the desired value. The desired value may, for example, be 5 kOhms. When the impedance is below the desired value, the skin region for the next electrode may be prepared by abrading the skin and the electrode subsequently applied electrode, and the impedance tested. This method may be repeated until all of the electrodes are successfully applied.

The electrodes 1-5 comprise a first sensing electrode 1, second sensing electrode 2 and third sensing electrode 3, a drive electrode 4 and a common electrode 5. Each of the first, second and third sensing electrodes 1, 2, 3 and the drive electrode are arranged around the reference feature 17 of the patch, in this embodiment equi-angularly spaced at about the same distance from the reference feature 17. Specifically, in the orientation shown in FIG. 1, the first and third sensing electrode 1, 3 are respectively to the left and right of the reference feature, and the second sense electrode 2 and the drive electrode 4 are respectively above and below the reference feature. The length of the tracks 15 connecting each of the electrodes 1-4 to the module 16 is thereby minimised, reducing any potential for noise (which may arise from electromagnetic interference, triboelectric effects etc).

In the embodiment the circular regions 21, 23 respectively associated with the first and third sensing electrode 1, 3 are arranged symmetrically on a horizontal line passing through the centre of the reference feature 17. The circular regions 22, 24 respectively associated with the second sensing electrode 2 and drive electrode 4 are arranged on a vertical line passing through the centre of the reference feature 17.

The circular region associated with the common electrode 5 is arranged on the vertical line passing through the reference feature 17, below the drive electrode 4. The drive electrode can be placed on any other part of the abdomen.

Each of the first and third sensing electrodes 1, 3 and the common electrode 5 are attached to the region of the substrate 100 that carries the reference feature 17 by a respective flexible substructure 13a, 13b, 13c. Each flexible substructure 13a-13c is attached at a first end to a part of the substrate 100 that carries the reference feature 17, and at a second end to the circular region 21, 23, 25. Each flexible substructure is arranged to deform so as to allow the relative positions of the first and second end of each flexible substructure to be adjusted when the substrate is conformed to a surface (such as an abdomen), thereby altering the positions of the electrodes 1, 3, 5, relative at least one of: each other, the other electrodes 2, 4, and the reference feature 17. In other embodiments a similar flexible substructure can be used to connect electrodes 2 and 4 to the part of the substrate 100 that carries the reference feature 17. Such an arrangement may accommodate transverse (horizontal) stretching of the skin.

In this arrangement, the flexible substructures 13a and 13b allow adjustment of the distance between the first sensing electrode 1 and the reference feature 17 and the distance between the third sensing electrode 3 and the reference feature 17. The ability of the substrate to accommodate adjustment of the positions of these electrodes makes the patch more comfortable, because the natural movement of the subject's skin (for instance as a result of breathing) can be accommodated by the flexible substructures 13a and 13b. A similar structure may be used in relation to electrodes 2 and 4. Furthermore, the patch may be configured to fit subjects with different sizes of abdomen, so that a single patch can be used on a wide range of subjects.

Each flexible substructure 13a-13c in this embodiment comprises a serpentine arrangement, in which at least one folded elongate member is disposed substantially lateral with a direction of movement to be accommodated by the substructure. The stiffness of such a member is substantially proportional to the third power of its length, and the compliance of the substructures in each direction may readily be tailored by adjusting their length, or the number of folds in the serpentine substructure (each fold further increasing the compliance). Each substructure 13a-13c carries the conducting track 15 of the electrode associated therewith.

The flexible substructures 13a and 13b are similar, these being rotationally symmetric about the centre of the reference feature 17, and having a single folded elongate member (having an outward leg and a return leg), that extends in a substantially vertical direction. Horizontal relative movement between the first and third sensing electrode 1, 3 is thereby accommodated.

The substructure 13c that connects the common electrode 5 to the part of the substrate carrying the reference feature 17 is different, and has two folded elongate members 31, 32, each extending in a substantially horizontal direction. This substructure 13c is configured to accommodate a greater degree of relative movement than the other substructures 13a, 13b, so that the common, electrode can be positioned towards the symphis pubis at a range of gestational ages and for a range of different sized subjects. The terms 'horizontal' and 'vertical' will be understood as relative terms, and are not intended to refer to 'horizontal' and 'vertical' directions of an external reference frame.

Figure 2:
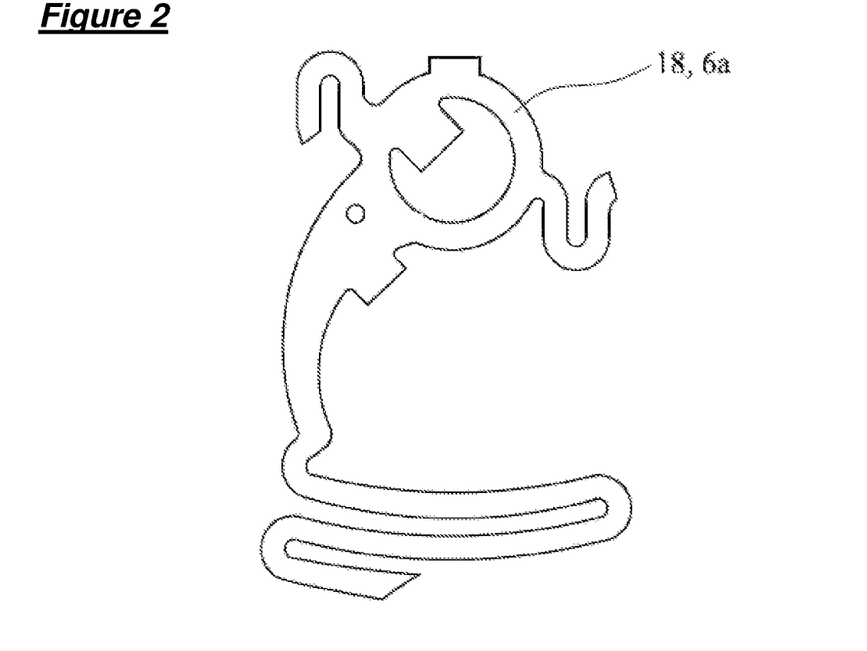
FIG. 2 is a layout diagram of the overlaminate layer of the embodiment of FIG. 1.

FIG. 2 shows the shape of the overlaminate layer 6a, and substantially corresponds with the shape of the substrate 100, but with the circular regions 21-25 omitted.

Figure 3:
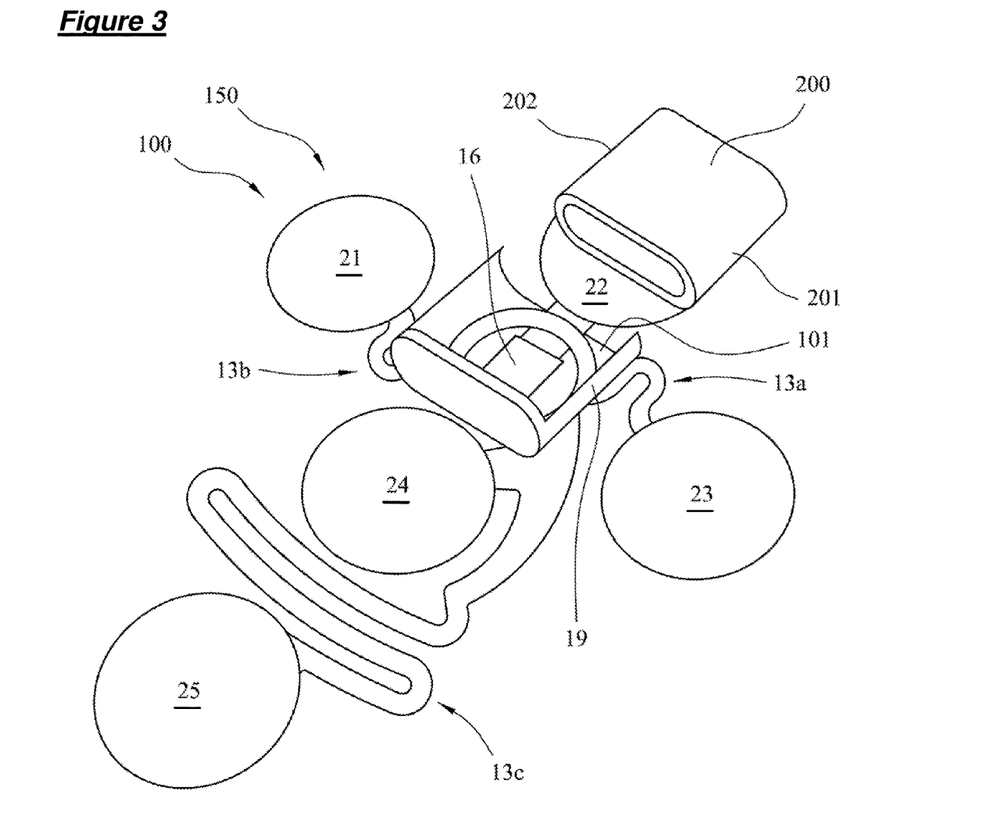
FIG. 3 is a perspective view of a patch and readout device according to an embodiment of the invention.

FIG. 3 shows a further patch according to an embodiment, comprising the same flexible substrate 100 that is shown in FIG. 1, with a mechanical module unit 19 affixed to the substrate 100 adjacent to the electrical module unit 16. The patch 150 is shown with a separate electronic readout device 200 for detecting electrophysiological signals from the electrodes 1-5 of the patch.

The electronic readout device 200 comprises a readout device housing 201 which is substantially cuboidal in shape, and which has an upper face 202 which is substantially square. The upper face 202 is similar in extent to one of the circular regions 21-25 associated with each readout electrode. The thickness of the housing 201, in a direction normal to the upper face 202, is less than half the edge length of the upper face 202, so that the readout device 200 is compact and low profile.

The mechanical module 19 comprises a cradle for receiving the readout device housing 201 of the readout device 200. The housing 201 is removably received and held within the cradle, which allows movement of the housing 201 only in the direction of insertion/removal. The cradle comprises a stop, and the readout device 200 is fully engaged with the mechanical module unit 19 when the housing 201 is in contact with the stop. The mechanical module 19 further comprises a latch or catch to retain the readout device housing 201 in contact with the stop. In this embodiment the latch or catch comprises a magnetic catch. A permanent magnet is provided on either (or both) of the mechanical module 19 and housing 201, which attracts a corresponding magnet (or ferromagnetic element) on the other of the mechanical module 19 or housing 201. In alternative embodiments, a hook and loop arrangement (e.g. Velcro) may be used to secure the readout device 200 to the patch 150.

Figure 5:
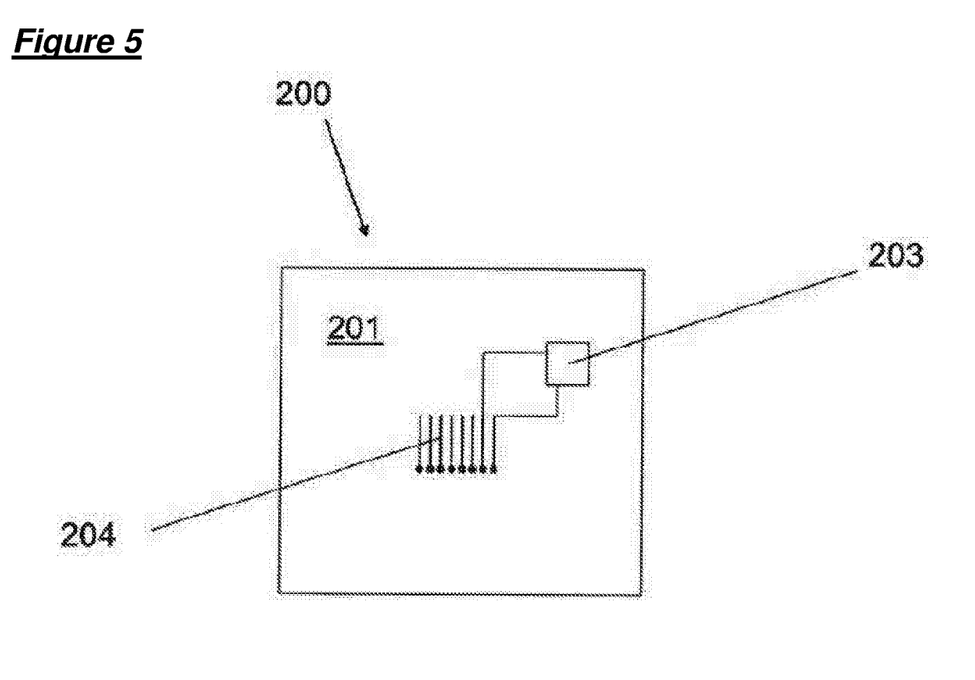
FIG. 5 is a schematic of a readout device according to an embodiment of the invention.

When the readout device housing 201 is fully engaged with the mechanical module 19, an electrical module 204 (shown in FIG. 5) of the readout device 200 is in electrical engagement with the electrical module 16 of the patch 150. The electrical module 204 of the readout device 200 may conveniently comprise a plurality of contacts mounted on resiliently deformable members (e.g. spring loaded contact pins).

The quality and reliability of the electrical contacts made to the module may be important when detecting electrophysiological signals (which are typically sub microvolt) and also for ensuring that stringent cleaning procedures associated with a hospital environment can be implemented on the readout device 200. Planar connections on the readout device 200 and resiliently biased connections on the patch 150 may be used. This arrangement allows easy cleaning of the readout device 200. The patch 150 may be disposed of after each use and hence not require cleaning, so the difficulty of cleaning the resiliently biased connections may not arise. Alternatively, either electrical module 204, 16 (of readout device 200 or patch 150) may comprise resiliently biased contacts wherein each contact pin resides inside a tube with a secure seal between the tube and the contact pin. The pins and their respective tubes may be are separated from each other by a sufficient distance to enable them to be cleaned. In this way the readout device 200 may be provided with resiliently biased contacts that may be readily cleaned.

In some situations it may be advantageous to seal the connected electrical modules 204, 16, for example to prevent the ingress of water or other fluids during a water birth delivery. One way to achieve this is to use a seal element (such as an O ring seal) around the electrical module 204, 16. The seal element may be provided on either the patch 150 or the readout device 200. The seal element may compressed when the readout device 200 is engaged with the mechanical module 19. The mechanical module 19 may be configured to urge the seal element into sealing engagement with the patch 150 and/or readout device 200 (for example by magnetic force).

A security device 101 is provided on the patch 150, for authenticating the patch 150 to the electrical readout device 200. In this embodiment the security device 101 is provided in the cradle. When the respective electrical modules 16, 204 of the patch 150 and readout device 200 are engaged, the readout device 200 checks the patch to determine whether it is authentic (i.e. checks whether the patch is an unauthorised copy). The authentication is achieved by communication (e.g. electrical, optical, wireless) between a security device 203 of the readout 200, and a corresponding security device 101 of the patch. The security devices 101, 203 may be configured to use cryptographic and/or hash functions.

Each electrical module 16, 204 may comprise nine connections. Three connections may be provided for each of three sensing electrodes, and a common and drive connection may be provided for the common and drive electrode respectively. A connection may be provided for connection to at least one conducting shield layer of the patch. A further three connections may be provided for connection with the security device, or chip, 101 of the patch 150.

The readout device 200 is preferably configured to determine and output at least one of a: fetal heart rate, fetal ECG, maternal heart rate, maternal ECG, or uterine activity. Preferably the readout device is configured to output any two, three, four, or all five of the above. The readout device is preferably configured to transmit the output, so that it can be monitored. Preferably, the readout device 200 comprises a wireless transmitter (e.g. according to the Bluetooth standard), operable to transmit the output of the readout device 200.

In some embodiments, the readout device 200 does not determine any of a fetal heart rate, fetal ECG, maternal heart rate, maternal ECG, or uterine activity, but instead transmits raw or partially processed voltage and/or current data from the electrodes, for processing by a further device into a suitable output (such as one, two, three, four or more of a fetal heart rate, fetal ECG, maternal heart rate, maternal ECG, or uterine activity).

Figure 7:
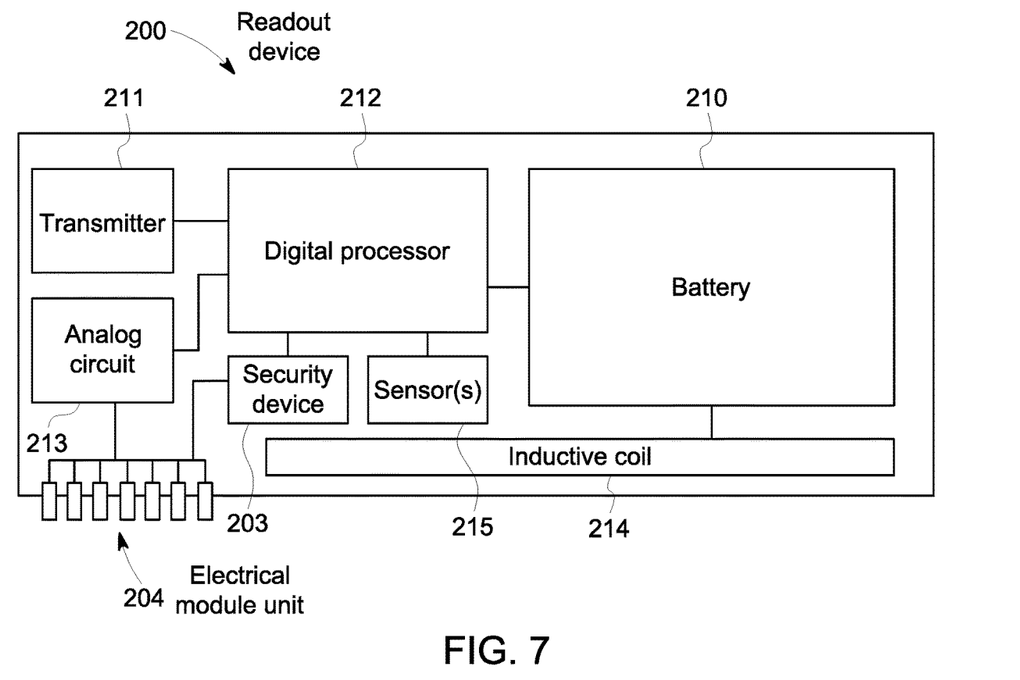
FIG. 7 is a block diagram of a readout device according to an embodiment of the invention.

Referring to FIG. 7, a block diagram of a readout device 200 according to an embodiment is shown. The readout device 200 comprises an electrical module unit 204, analogue circuit 213, digital processor 212, wireless transmitter 211, security device 203, battery 210 and inductive coil 214.

The analogue circuit 213 comprises an analogue to digital converter, and receives the electrical signals from the electrodes, and outputs a digitised version thereof, for processing by the digital signal processor. In some embodiments the analogue circuit 213 may comprise an amplifier and/or filter.

The processor 212 receives a digitised signal from the analogue circuit 213, and preferably processes it to determine an output, as described already. The processor 212 subsequently outputs a signal to the wireless transmitter 211 for onward transmission, for example to a receiving and display station 300 according to an embodiment of the invention.

In order to maximise the battery life of the removable electronic device it may be configured such that the power of the wireless transmitter is controlled based upon the signal strength index and/or bit error rate. This may greatly lengthen the monitoring period that can be carried under one single battery charge.

In some embodiments, one or more component of the device 200 may be combined, for example in a multi-chip module or system on chip. For example, the processor 212 may comprise any combination of the analogue circuit 213, the security device 203 and the wireless transmitter 211.

The electronic components of the readout device 200 are powered by an electrical power source, which is a battery 210 in this embodiment. In other embodiments the electrical power source may comprise a capacitor. The inductive coil 214 is operative to charge the battery 210, optionally under the control of the processor 210.

The readout device 200 may be configured to detect electrophysiological signals between a pair of sensing electrodes, rather than simply between a sensing electrode and the common electrode. For example, the readout device 200 may be configured to detect electrophysiological signals between sensing electrodes 1 and 3 (i.e. horizontally across the abdomen in use). This allows a further channel of UA and fetal ECG to be provided. The advantages for UA are that the separation is relatively fixed between electrodes 1 and 3 and hence this offers the potential of indicating contraction strength. Furthermore such a horizontal fECG channel (measured between sensing electrodes 1 and 3) allows breech and transverse presentations to be more carefully monitored. In addition, by providing this channel a further Maternal ECG channel can be generated that can be used for mECG removal, further reducing confusion between the mECG and fECG. Such confusion is a common problem with Doppler ultrasound whereas with abdominal fECG the percentage confusion time is considerably reduced. The use of another mECG channel (for example, measured between sensing electrodes 1 and 3) can further reduce this confusion by providing an improved template for accurate mECG removal.

The readout device 200 may comprise sensors 215, which may comprise an inertial sensor such as accelerometer and/or gyroscope. Preferably, the sensors 215 comprise a one, two or three axis accelerometer, and/or a one, two or three axis gyroscope. The sensors 215 may be MEMS (micro-electromechanical systems) devices. The readout device 200 may comprise an inertial measurement unit. The accelerometers and gyroscopes may be used to track the movement of the readout device 200, thereby allowing both fetal ECG and electrohysterogram algorithms to differentiate between maternal/fetal movements and genuine contractions and fetal ECG signals. A gyroscope can provide useful additional rotational information that an accelerometer cannot provide, thereby allowing further separation of fetal movement from the acquired data. This fetal movement is a highly useful indicator that provides further fetal well-being indication. Additionally the use of the pair of devices allows separation of the maternal breathing signal which is a further indication of maternal health.

Figure 4:
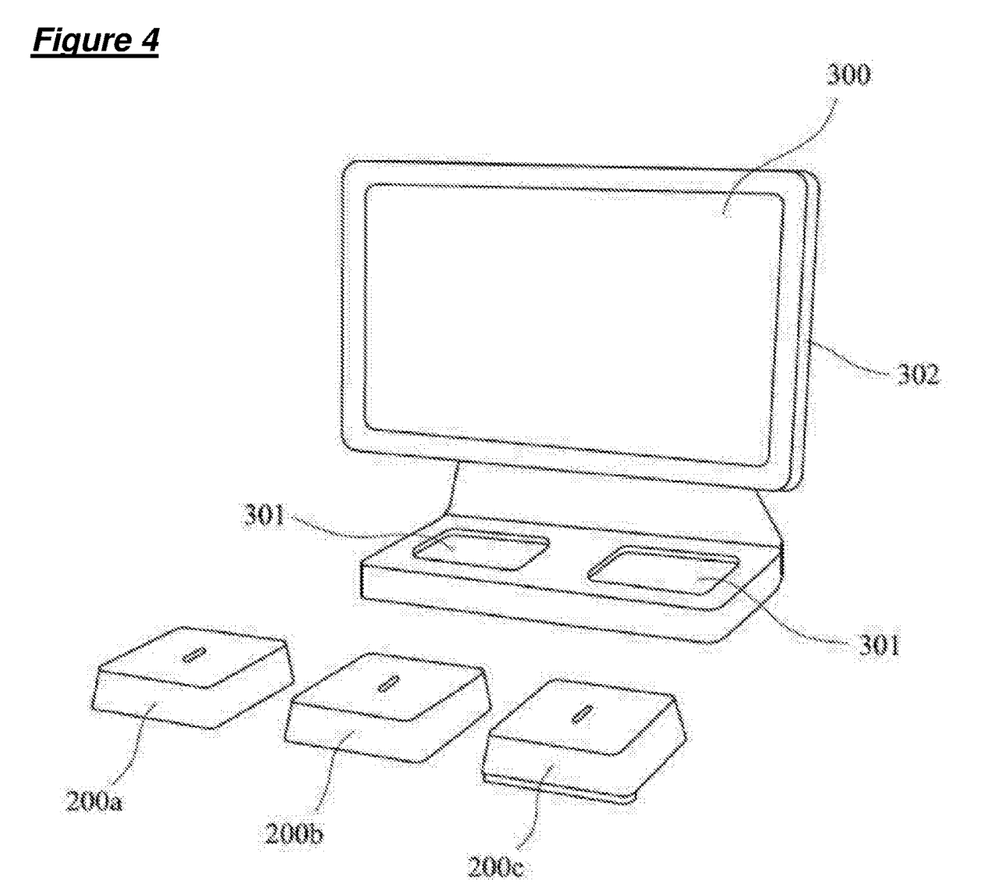
FIG. 4 is a perspective view of a receiving station according to an embodiment of the invention, with three different embodiments of a readout device according to an embodiment of the invention.

In FIG. 4, a signal receiving and display station 300 is shown, comprising a screen 302, and two dock areas 301. The receiving station is operable to receive and display output signals from the readout device 200 on the screen 302. The dock areas 301 are arranged to receiving part of the housing 201 of the readout device 200, and are provided with a wireless charging device, that is operable to charge a readout device 200 placed in the dock area 301. The wireless charging device preferably operates by inducing a current in a conductor of the readout device 200 using a coil. A number of alternative embodiments 200a, 200b, 200c of readout devices 200 are shown in front of the receiving station, each having slightly different designs of housing 201. The housing 200 is preferably waterproof, and is preferably IP57 rated.

The receiving and display station 300 can have two significant functions. The first is to display the full set of fetal and maternal parameters (i.e. FHR, MHR, UA, fetal movement etc) to the clinical care team or community midwife. A second significant function is that of an interface device that connects to existing installed CTG (cardiotocograph) machines. This latter function allows hospitals/health care units to efficiently use its existing resources without making equipment redundant whilst benefiting from the advantages of abdominal electrophysiological monitoring i.e. increased FHR accuracy; improved reliability of FHR/UA with BMI; maternal mobility; reduced FHR/MHR confusion etc.

At least two readout devices 200 are preferably allotted for a single patient. When one readout device 200 is connected to the patch 150 it sends the patch unique ID to the receiving and display station 300 so that the second readout device 200 can only be connected to the same patch 150 when the readout devices 200 are eventually swapped over. Readout devices may be swapped when the battery becomes discharged or when routine maintenance is required. The number of readout devices 200 associated with each patient, patch, or receiving and display station 300 is not limited to two or three (as shown in FIG. 4) as labour or a maternal antenatal recording session can extend over a considerable time, for example from a few hours to several weeks.

The use of at least two readout devices 200 allows a seamless swapping of the readout devices 200. The subsequent readout device 200 may already have the appropriate patch ID loaded into its local memory so as to reduce set up time.

Figure 6:
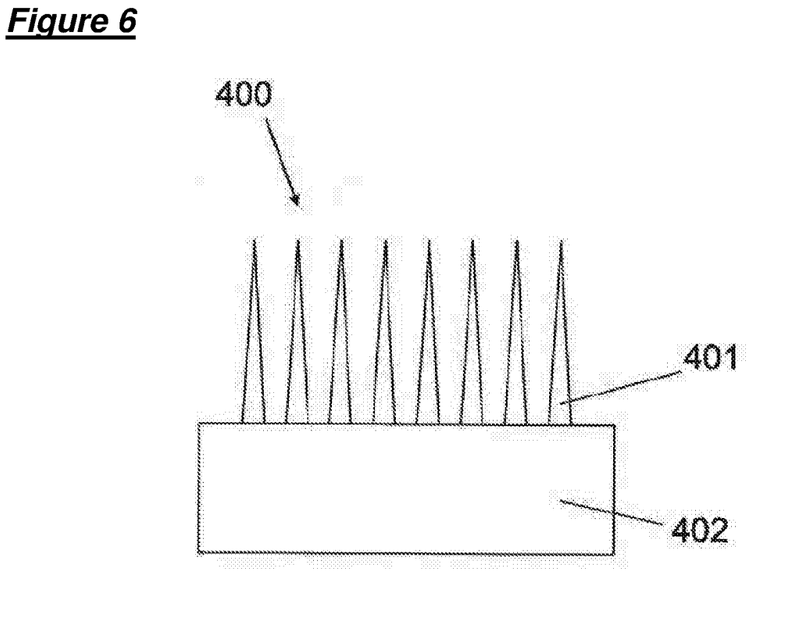
FIG. 6 is a sectional schematic of an electrode according to an embodiment of the invention.

Referring to FIG. 6, an electrode 400 is shown. The electrode 400 is for use as an electrode of a patch according to an embodiment of the invention, and comprises a substrate 402, from which extend a plurality of electrically conductive needles 401. The needles are formed from a bio-compatible material (such as doped silicon), and are configured to penetrate the stratum corneum to provide an electrical connection to the more conductive underlying layers, without penetrating far enough to stimulate nerves so as to cause pain. The needles therefore have a length of between 20 μm and 200 μm, preferably between 50 μm and 100 μm. The needles may be formed by reactive ion etching or wet etching of silicon, or may be formed by any other suitable process, from any other suitable material. The electrode 400 may be used as each electrode of a patch according to an invention. A patch 150 that comprises such electrodes 400 may obviate the careful preparation of the skin that is usually necessary to achieve a low enough impedance contact to the subject, because the needles facilitate contact to be made through the stratum corneum.

Figure 8:
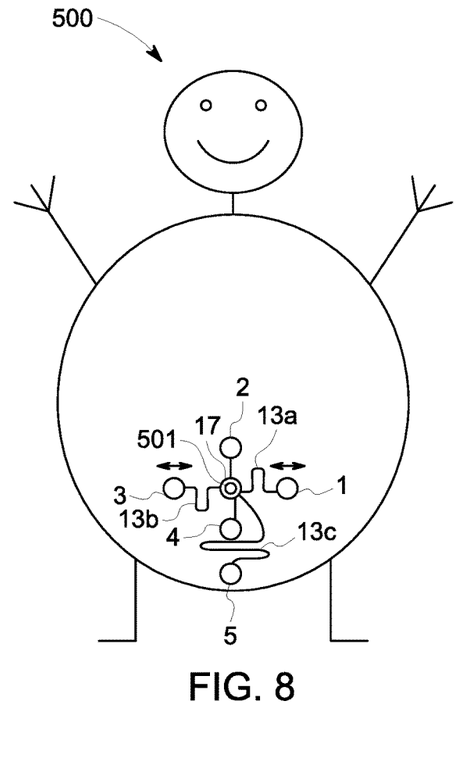
FIG. 8 is a schematic of a test subject and a patch according to an embodiment of the invention, in use on the subject.

Referring to FIG. 8, a patch 150 according to an embodiment of the invention is shown in use, applied to the abdomen of a pregnant human subject 500. The skin is preferably prepared to ensure a good contact is made between each electrode and the skin, and gel is preferably applied to electrically couple the electrodes to the skin. The reference feature 17 of the patch is aligned with the umbilicus 501 of the subject 500, and the first sensing electrode 1 and drive electrode 4 are arranged on the abdomen on the median plane of the subject. The common electrode 5 is placed facing the symphis pubis, by extending the flexible substructure 13c if necessary. The patch 150 is comfortable and low profile, and relative movement of the electrodes (e.g. as a result of breathing and locomotion) is accommodated.

The readout device 200 is engaged with the module of the patch 150, so that their respective electrical modules 16, 204 are connected. In order for the readout device to work with the patch 150, and provide any useful output, the patch is preferably first authenticated by the readout device, using the respective security devices 101, 203.

Once the patch 150 is authenticated, the readout device 200 amplifies and filters the electrophysiological signals detected by the sensing electrodes 1-3 to determine and output all of: a fetal ECG, a fetal heart rate, a maternal ECG, a maternal heart rate, and a uterine activity. More specifically, the voltage difference between the sensing electrodes and the common electrode is sensed and processed by the readout device to create an output signal from the readout device 200. The common mode voltage of the three sense electrodes 1-3 is applied to the shield layers 9a, 9b of the patch 150, to minimise leakage currents to the shield layers. The inverse of the common mode voltage is applied to the drive electrode 4 to minimise common mode voltage noise. The term 'common mode' is used in the conventional sense of a signal that is shared by more than one conductor.

The integration of the readout circuit 200 and patch 150 allows the subject to move freely, without having to worry about leads, and minimising any deleterious cable noise that can arise due to triboelectric effects when leads are flexed.

Furthermore, the short length of the connections to the readout circuit minimise the potential for other sources of noise.

The readout device 200 preferably comprises a wireless transmitter (not shown), and is operable to wirelessly transmits the output, via the wireless transmitter, substantially in real time, to a monitoring station that is operable to display the output. The readout device 200 is compatible with a number of monitoring stations, but is preferably used with a receiving and display station 300 according to an embodiment of the invention.

When the need for monitoring abdominal electrophysiological signals has passed, the readout device 200 is removed from the patch 150, and the patch can disposed of. The readout device 200 can be subsequently re-used with a different patch 150, preferably after the readout device 200 is sterilised (e.g. by immersion in a sterilising fluid). The patch 150 may therefore be made relatively cheaply, and the readout device 200 may include relatively sophisticated electronics without compromising the cost of using the system. When the readout device 200 is not in use with a patch 150, it may preferably be placed on a docking area 301 of the receiving and display station 300, so that it charges ready for another use. There may be two or more readout devices 200 associated with each monitoring station 300, so that one readout device 200 is always charging while the other is in use, thereby ensuring that a charged device is always ready for use.

It will be appreciated that the patch, readout, monitoring device and systems comprising combinations of these address a number of the problems with prior art devices.

Although an embodiment of the patch has been described in which each flexible substructure comprises a serpentine flexure, any suitable arrangement may be used. For example, in some embodiments the flexible substructure may comprise a corrugated region of the substrate that can accommodate movement parallel to the plane of the substrate. Other compliant planar arrangements may also be used. For example, the electrode may be coupled to the remainder of the patch via a ring shaped element, wherein the ring has geometry selected (e.g. large diameter, narrow width) to accommodate movement in the plane of the substrate.

In any examples of the invention, the patch may be provided with a backing material layer which is removable, e.g. by peeling, to expose the patch adhesive region(s) for attachment of the patch to the abdomen of a wearer. Separate or individual backing sheets may be applied to different electrodes/portions of the patch such that individual portions can be adhered and/or replaced as necessary.

A number of other modifications and variations may be made, without departing from the scope of the invention, as defined by the appended claims.

The invention claimed is:

1. A multi-electrode patch for abdominal detection of fetal electrophysiological signals, the patch comprising:
   a flexible substrate comprising at least four electrodes, the flexible substrate including a center region and at least four electrode regions connected to and extending out from the center region, each electrode region including one of the at least four electrodes;
   wherein the at least four electrodes include at least three sensing electrodes disposed along an arc around the center region and a common electrode disposed below the center region;
   wherein the common electrode is connected to the center region by a flexible substructure that is extendable such that a relative position of the common electrode can be adjusted with respect to the center region based on a size of a mother's abdomen and a position of a fetus; and
   an electronic readout device removably mounted on the flexible substrate and configured to detect fetal electrophysiological signals from the at least four electrodes based on voltage differences between the common electrode and each of the at least three sensing electrodes.

2. The patch of claim 1, wherein the flexible substructure has an arched, serpentine or corrugated portion, such that the relative positions of at least some of the at least three sensing electrodes relative to each other on the surface can be adjusted by moving the at least some of the at least three sensing electrodes and deforming the flexible substrate.

3. The patch of claim 2, wherein the flexible substrate further comprises a reference feature for alignment with an umbilicus, and the flexible substructure allows a distance along the surface from the reference feature to the at least one of the at least three sensing electrodes to be adjusted.

4. The patch of claim 1, wherein the flexible substrate comprises a conducting layer and a first insulating layer, and a first graphite layer between the conducting layer and the insulating layer.

5. The patch of claim 4, wherein the patch comprises a plurality of conducting layers, the plurality of conducting layers comprising:
   a signal layer, for communicating electrical signals from the at least four electrodes; and
   a first shield layer, for shielding the signal layer from electromagnetic interference;
   wherein the first shield layer is separated from the signal layer by the first graphite layer and the first insulating layer.

6. The patch of claim 5, wherein the first shield layer is disposed adjacent to a first side of the signal layer, and the plurality of conducting layers comprises a further shield layer disposed adjacent to a second side of the signal layer, wherein the further shield layer is separated from the signal layer by a further graphite layer and a further insulating layer.

7. The patch of claim 5, wherein an outer insulating layer is disposed adjacent to an outward facing side of at least one of the first shield layer and the further shield layer.

8. The patch of claim 1, wherein at least one electrode of the at least four electrodes comprises a plurality of electrically conducting biocompatible needles, wherein each needle of the plurality of biocompatible needles has a length between 10 μm and 200 μm.

9. The patch or electrode of claim 8, wherein each of the plurality of biocompatible needles has a mean diameter of between 10 μm and 100 μm.

10. The patch of claim 8, wherein an areal density of the plurality of biocompatible needles is between 200 and 1000 needles per square millimetre.

11. The patch of claim 8, wherein the plurality of biocompatible needles are configured to penetrate a median thickness of the stratum corneum of the abdomen of a pregnant human.

12. The patch of claim 1, wherein a first and third sensing electrode of the at least three sensing electrodes are each connected to the center region by a respective one of a plurality of flexible substructures.

13. The patch of claim 12, wherein a second sensing electrode of the at least three sensing electrodes between the first and third sensing electrodes is a fixed distance from the center region and is not connected to the center region by a flexible substructure.

14. The multi-electrode patch of claim 1, further comprising a module unit mounted on the flexible substrate for removably engaging with the electronic readout device, wherein the module unit is configured to support the electronic readout device on the flexible substrate;
wherein the module unit comprises a mechanical module unit for removable mechanical engagement with a housing of the readout device, and an electrical module unit for making an electrical connection from the at least four electrodes to the readout device; and
wherein engaging the patch with the readout device comprises engaging both the mechanical module unit and the electrical module unit.

15. The multi-electrode patch of claim 14, wherein the module unit is mounted on the center region of the flexible substrate.

16. The patch of claim 14, wherein the mechanical module unit comprises a magnet or ferromagnetic material.

17. The patch of claim 14, wherein the mechanical module unit comprises a cradle that is mechanically engaged with the housing by sliding at least part of the housing into the cradle.

18. A multi-electrode patch for abdominal detection of fetal electrophysiological signals, the patch comprising:
a flexible substrate comprising a center region and a plurality of electrodes extending out from the center region and configured to be placed around an umbilicus of a mother's abdomen to detect electrophysiological signals of a fetus, wherein the plurality of electrodes include:
a common electrode and a first sensing electrode configured to be positioned along a median line through the mother's umbilicus, where the common electrode is configured to be positioned below the mother's umbilicus and the first sensing electrode configured to be positioned above the mother's umbilicus; and
at least two lateral side sensing electrodes, one positioned on each lateral side of the median line;
wherein of the common electrode is connected to the center region via a flexible substructure that is extendable such that a relative distance between the common electrode and the first electrode can be adjusted based on at least one of a size of the mother's abdomen and a position of the fetus; and
an electronic readout device removably mounted on the flexible substrate and configured to detect the fetal electrophysiological signals based on voltage differences between the common electrode and each of the sensing electrodes.

19. The multi-electrode patch of claim 18, wherein at least one of the at least two lateral side electrodes is connected to the center region via a flexible substructure such that a relative distance between the common electrode the respective side electrode can be adjusted based on at least one of the size of the mother's abdomen and the position of the fetus.

20. The multi-electrode patch of claim 18, wherein the first sensing electrode and the two lateral side electrodes are disposed along an arc around the center region.

21. The multi-electrode patch of claim 18, wherein the electronic readout device is removably mounted on the center region of the flexible substrate by a module unit; and
wherein the flexible substrate further includes a reference feature for alignment with an umbilicus of the mother and wherein the module unit is configured to removably mount the electronic readout device on the center region over the umbilicus of the mother.

22. The multi-electrode patch of claim 18, wherein the readout device further comprises an inertial sensor configured to detect at least one of maternal movement, maternal breathing, maternal contraction and fetal movement.

23. The multi-electrode patch of claim 22, wherein the readout device is configured to utilize the detected at least one of maternal movement, maternal breathing, maternal contraction and fetal movement from the inertial sensor to reduce artefacts in at least one of a fetal heart rate and a fetal ECG electrocardiographic (ECG) output.

24. The multi-electrode patch of claim 18, wherein the readout device comprises a wireless transmitter, and wherein the readout device is operable to wirelessly transmit an output comprising at least one of a fetal heart rate, a fetal ECG, and uterine activity.

25. The multi-electrode patch of claim 24, wherein the readout device is further configured to transmit an output further comprising at least one of a maternal heart rate and a maternal ECG.

26. The multi-electrode patch of claim 18, wherein at least one of the plurality of electrodes comprises a plurality of electrically conducting biocompatible needles of a length of between 10 μm and 200 μm such that the plurality of electrodes can be placed on the mother's abdomen to detect the electrophysiological signals of the fetus without first preparing the skin by removing a region of the stratum corneum.

27. A multi-electrode patch for abdominal detection of fetal electrophysiological signals, the patch comprising:
a flexible substrate comprising a center region and a plurality of electrodes extending out from the center region and configured to be placed in an arc around an umbilicus of a mother's abdomen to detect electrophysiological signals of a fetus;
wherein the plurality of electrodes include a common electrode and a plurality of sensing electrodes, wherein the common electrode is configured to be positioned below the mother's umbilicus and at least one of the sensing electrodes is configured to be positioned above the mother's umbilicus;
a flexible substructure connecting the common electrode to the center region, wherein the flexible substructure is extendable so as to adjust a relative position of the common electrode with respect to the center region based on a size of the mother's abdomen and a position of the fetus;
an electronic readout device removably mounted on the flexible substrate and configured to detect the fetal electrophysiological signals based on voltage differences between the common electrode and each of the sensing electrodes.

28. The multi-electrode patch of claim 27, wherein and one or more of the sensing electrodes are connected to the center region via a flexible substructure such that a relative distance between the sensing electrode and the center region can be adjusted based on at least one of a size of the mother's abdomen and a position of the fetus.

29. The multi-electrode patch of claim 27, wherein the center region includes a reference feature for alignment with the mother's umbilicus.

30. The multi-electrode patch of claim 29, wherein the center region is configured to surround the mother's umbilicus.

31. The multi-electrode patch of claim 30, further comprising a module unit configured to removably mount the electronic readout device on the center region over the mother's umbilicus.

32. The multi-electrode patch of claim 27, wherein the plurality of sensing electrodes comprises an upper sensing electrode configured to be positioned above the mother's umbilicus and at least two lateral side sensing electrodes, one positioned on each lateral side of a median line through the mother's umbilicus.

33. The multi-electrode patch of claim 32, wherein each lateral side electrode is connected to the center region via a respective flexible substructure such that a relative position of each lateral side electrode is adjustable relative to the mother's umbilicus.

34. The multi-electrode patch of claim 33, wherein the upper sensing electrode is connected at a fixed distance from the center region.

\* \* \* \* \*